(12) United States Patent
Kosterev

(10) Patent No.: US 7,245,380 B2
(45) Date of Patent: Jul. 17, 2007

(54) QUARTZ-ENHANCED PHOTOACOUSTIC SPECTROSCOPY

(75) Inventor: Anatoliy A. Kosterev, Houston, TX (US)

(73) Assignee: William Marsh Rice University, Houston, TX (US)

( * ) Notice: Subject to any disclaimer, the term of this patent is extended or adjusted under 35 U.S.C. 154(b) by 178 days.

(21) Appl. No.: 10/517,177

(22) PCT Filed: Jun. 10, 2003

(86) PCT No.: PCT/US03/18299

§ 371 (c)(1),
(2), (4) Date: Feb. 15, 2005

(87) PCT Pub. No.: WO03/104767

PCT Pub. Date: Dec. 18, 2003

(65) Prior Publication Data

US 2005/0117155 A1    Jun. 2, 2005

Related U.S. Application Data

(60) Provisional application No. 60/389,580, filed on Jun. 18, 2002, provisional application No. 60/387,488, filed on Jun. 10, 2002.

(51) Int. Cl.
*G01N 21/00* (2006.01)
(52) U.S. Cl. ....................... 356/437; 250/343
(58) Field of Classification Search ............ None
See application file for complete search history.

(56) References Cited

U.S. PATENT DOCUMENTS

| | | | | |
|---|---|---|---|---|
| 3,911,276 A | * | 10/1975 | Bell | 250/343 |
| 4,068,125 A | * | 1/1978 | Bell | 356/73 |
| 4,412,445 A | * | 11/1983 | Spellicy | 73/24.02 |
| 4,457,162 A | * | 7/1984 | Rush et al. | 73/24.01 |
| 4,535,241 A | * | 8/1985 | Eberhardt | 356/437 |
| 4,713,540 A | * | 12/1987 | Gilby et al. | 250/227.21 |
| 4,817,413 A | * | 4/1989 | Asano et al. | 73/24.02 |
| 5,159,411 A | | 10/1992 | Hammerich et al. | |
| 6,236,455 B1 | | 5/2001 | Autrey et al. | |
| 6,244,101 B1 | | 6/2001 | Autrey et al. | |
| 6,348,968 B2 | | 2/2002 | Autrey et al. | |
| 6,466,806 B1 | | 10/2002 | Geva et al. | |
| 6,694,173 B1 | * | 2/2004 | Bende et al. | 600/473 |
| 7,101,340 B1 | * | 9/2006 | Braun | 73/23.3 |

OTHER PUBLICATIONS

PCT International Search Report for International Application No. PCT/US03/18299, dated Dec. 6, 2004 (2 p.).
Photoacoustic Spectroscopy [online] Retrieved from the Internet:<URL: http://nte-serveur.univ-[yon].fr/nte/specrtoscopic/photoaccoustiques/Web_PASS.htn dated May 2003.
Photoacoustic Spectroscopy [online] Retrieved from the Internet:<URL: http:/www.uni-hohenheim.de/~wwwgkoll/teilpr/Raimunde/node3.html dated May 8, 2003.

(Continued)

*Primary Examiner*—Layla G. Lauchman
*Assistant Examiner*—Juan D. Valentin, II
(74) *Attorney, Agent, or Firm*—Conley Rose, P.C.

(57) ABSTRACT

Methods and apparatus for detecting photoacoustic signals in fluid media are described. The present invention differs from conventional photoacoustic spectroscopy in that rather than accumulating the absorbed energy in the fluid of a sample cell, the absorbed energy is accumulated in an acoustic detector or sensitive element. In a preferred embodiment, the acoustic detector comprises piezoelectric crystal quartz. The quartz is preferably in the shape of a tuning fork.

13 Claims, 4 Drawing Sheets

OTHER PUBLICATIONS

Quartz Clock [online] Retrieved from the Internet:<URL: http://www.wikipedia.org/w/wiki/phtml?title+Quartz_clock&printable=yes dated May 19, 2003.

What! Quartz Tuning Forks? [online] Retrieved from the Internet:<URL: http://members.iinet.net.au/~fotoplot/accqf.htm dated May 27, 2003.

Grober et al., *Fundamental limits to force detection using quartz tuning forks*, Review of Scientific Instruments vol. 71, No. 7 dated Jul. 2000 (pp. 2776-2780).

Shen et al., *Time Resolved Aspects of Pulsed Photoacoustic Spectroscopy*, Analytical Sciences Apr. 2001, Vo. 17, Special Issue 2001.

Gunther et al.; *Scanning Near-Field Acoustic Microscopy*: Applied Physics B 48, 89-92 (1989).

Karrai et al., *Piezoelectric tip-sample distance control for near field optical microscopes*, Applied Phys. Lett. 66 (14), Apr. 3, 1995.

Kosterev et al., *Quartz-enhanced photoacoustic spectroscopy*, Optics Letters, vol. 27, No. 21, Nov. 1, 2002; 1902-1904.

\* cited by examiner

QUARTZ-ENHANCED PHOTOACOUSTIC SPECTROSCOPY

STATEMENT REGARDING FEDERALLY SPONSORED RESEARCH OR DEVELOPMENT

None.

FIELD OF THE INVENTION

The present invention generally relates to the field of photoacoustic spectroscopy. More specifically, the present invention relates to detecting photoacoustic signals in a fluid and accumulating the signals in an acoustic detector.

BACKGROUND OF THE INVENTION

Photoacoustic spectroscopy (PAS) is an analytical method that involves stimulating a sample by light and subsequently detecting sound waves emanating from the sample. Typically, only a narrow range of wavelengths of light are introduced into a sample. Such narrow range of wavelengths of light can be formed by, for example, a laser. Utilization of only a narrow range of wavelengths can enable preselected molecular transitions to be selectively stimulated and studied.

A photoacoustic signal can occur as follows. First, light stimulates a molecule within a sample. Such stimulation can include, for example, absorption of the light by the molecule to change an energy state of the molecule. Second, an excited state structure of the stimulated molecule rearranges. During such rearrangement, heat, light, volume changes and other forms of energy can dissipate into an environment surrounding the molecule. Such forms of energy cause expansion or contraction of materials within the environment. As the materials expand or contract, sound waves are generated.

In order to produce a series of sound waves or photoacoustic signals, the light is pulsed or modulated, at a specific resonant acoustic or modulation frequency f. Accordingly, an acoustic detector mounted in acoustic communication with the environment can detect changes occurring as a result of the light stimulation of the absorbing molecule concentration or signal.

Because the amount of absorbed energy is proportional to the concentration of the absorbing molecules, the acoustic signal can be used for concentration measurements.

In typical PAS, a resonant acoustic cavity or sample cell with a quality factor Q is used to isolate and amplify sound wave signals, thereby increasing sensitivity of detection. The light intensity or wavelength is modulated at f. The absorbed energy is accumulated in the acoustic mode of the sample cell during Q oscillation periods. Hence, the acoustic signal is proportional to the effective integration or energy accumulation time t, where $t=Q/f$. Most often the Q factor is in the range 40–200 and $f=1,000–4,000$ Hz. For example, if $Q=70$ and $f=1250$ Hz, then $t=0.056$ s An exemplary prior art apparatus 10 for PAS is shown in FIG. 1. Apparatus 10 comprises a light source 12 configured to emit a beam of radiation into a sample holder 14. Light source 12 can comprise, for example, a laser. Filters (not shown) can be provided between light source 12 and sample holder 14 for attenuating the light prior to its impacting sample holder 14.

Sample holder 14 comprises a sample cell 18 containing a sample 16. Sample cell 18 can comprise a number of materials known to persons of ordinary skill in the art, and preferably comprises a material substantially transparent to the wavelength(s) of light emanating from light source 12. Preferred materials of sample cell 18 will accordingly vary depending on the wavelengths of light utilized in the spectroscopic apparatus.

Sample 16 comprises a material that substantially fills sample cell 18. Such material can be, for example, a fluid such as a liquid or a gas. Sample 16 can, for example, comprise a liquid solution wherein the molecular vibrations that are to be studied are associated with molecules dissolved in the liquid.

Apparatus 10 further comprises an acoustic detector 20 mounted to sample cell 18 and in acoustic communication with sample 16. Acoustic detector 20 can comprise a transducer, such as, for example, a microphone and can be mounted such that a fluid is provided between a surface of detector 20 and sample cell 18. Detector 20 is typically removably mounted to sample cell 18 by, for example, a clamp. Acoustic detector 20 is in electrical communication with an output device 22. Device 22 can be configured to display information obtained from detector 20, and can be further configured to process such information. Output device 22 can comprise, for example, an oscilloscope or a computer.

In operation, a beam of light is generated by source 12 and passed through sample cell 18 to stimulate molecular excitation within sample 16. Non-radioactive decay or molecular rearrangements cause expansions and/or contractions of a material within sample 16 to generate acoustic waves passing from sample 16 through sample cell 18 and to acoustic detector 20. Acoustic detector 20 then detects the acoustic waves and passes signals corresponding to, for example, amplitudes and frequencies of the acoustic waves to output device 22. Output device 22 can be configured to convert information obtained from detector 20 to, for example, a graphical display.

In this way the absorbed laser power is accumulated in the acoustic mode of sample cell 18 for Q acoustic oscillation periods before the sound waves decay. As can be appreciated, the dimensions of sample cell 18 are dependent upon f, where the size of the resonant sample cell cannot be less than half an acoustic wavelength, that is ~15 cm at $f=1,000$ Hz. Also, because PAS detectors are sensitive to environmental noise, additional buffer volumes are often added onto the sample cells to suppress background noise.

Achieving longer t's in a fluid-filled sample cell 18 is problematic because of sample cell dimension constraints in addition to intrinsic losses related to gas viscosity and other relaxation processes.

In order to achieve longer energy accumulation times (t's), and therefore better signals, a need exists for methods and apparatus that can detect changes occurring as a result of the light stimulation of an absorbing molecule without the use of a sample cell.

SUMMARY OF THE INVENTION

The present invention relates to methods and apparatus for measuring a fluid sample without the use of a resonant sample cell. The present invention differs from conventional PAS in that rather than accumulating the absorbed energy in the fluid of the sample cell, the absorbed energy is accumulated in an acoustic detector or sensitive element. In a preferred embodiment, the acoustic detector comprises piezoelectric crystal quartz.

These and other embodiments of the present invention, as well as their features and advantages, will become apparent with reference to the following detailed description.

BRIEF DESCRIPTION OF THE DRAWINGS

A better understanding of the present invention can be obtained when the following detailed description of the preferred embodiment is considered in conjunction with the following drawings, in which.

NOTATION AND NOMENCLATURE

Figure 1:
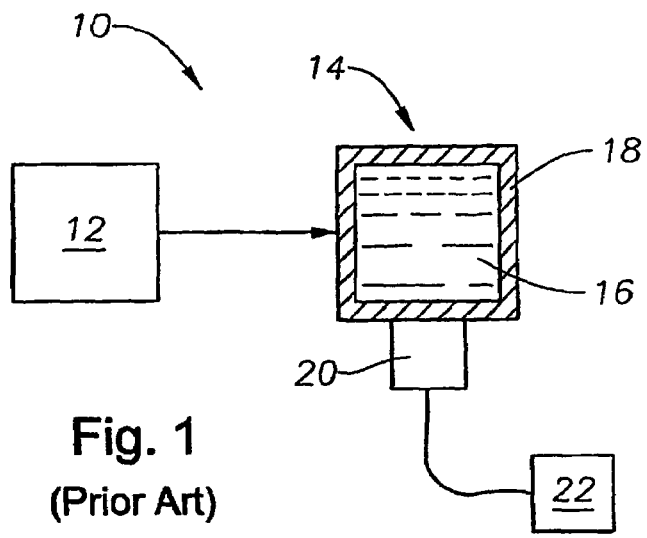
FIG. 1 is a schematic of a prior art apparatus for PAS.

In the following discussion and in the claims, the terms "including" and "comprising" are used in an open-ended fashion, and thus should be interpreted to mean "including, but not limited to . . . ." In addition, "preamplifier" is intended to relate to an amplifier designed to amplify extremely weak electrical signals before they are fed to additional amplifier circuits.

DETAILED DESCRIPTION OF THE PREFERRED EMBODIMENTS

As described above, in the present photoacoustic spectroscopy methods and apparatus, the absorbed energy from a fluid is accumulated in an acoustic detector or sensitive element. This is in contrast to conventional photoacoustic spectroscopy, where a sample cell houses a fluid sample and the fluid accumulates the absorbed energy.

In a preferred embodiment, the acoustic detector comprises a material selected from piezoelectric crystals. Preferably, the acoustic detector is piezoelectric crystal quartz.

Chemically, quartz is silicon dioxide. When quartz is properly cut, it will generate electric charge separation, resulting in electric field or current, when mechanical stress is applied to it; this property is known as piezoelectricity.

Many materials can be formed into shapes that resonate. However, since quartz deformation can be monitored directly by an electric signal, additional transducers are not needed.

As can be appreciated, piezoelectric crystal quartz is especially attractive for use in the present invention because it has extremely low intrinsic losses resulting in high Q, and is inexpensive. In addition, piezoelectric crystal quartz is abundantly available; nearly every electronic watch or clock is built around a high-Q quartz crystal frequency standard (i.e. a quartz tuning fork (TF) with a resonant frequency close to 32,768 (i.e. $2^{15}$) Hz). This frequency is sufficiently low to allow intermolecular excitation to be converted to sound waves in fluid at normal pressure. Quartz frequency standards are thermally compensated at room temperature, therefore resonant frequency f of a tuning fork comprised of quartz will be relatively stable as the temperature changes.

In accordance with principles of the present invention, a quartz tuning fork is used as an acoustic detector in PAS. This tuning fork-based PAS is hereinafter referred to as "quartz-enhanced photoacoustic spectroscopy", or QEPAS.

An important feature of QEPAS is its immunity to background acoustic noise, which is a consequence of the following:

The ambient acoustic noise density approximately follows a 1/f dependence and is very low above 10 kHz, The acoustic wavelength in air is ~1 cm at 32 kHz and longer at lower frequencies. Therefore, the sound waves emanating from a distant source tend to apply a force in the same direction to each of the two timing fork prongs positioned ~1 mm apart. This does not excite the piezoelectrically active mode, in which the two prongs move in opposite directions.

The width of the tuning fork resonance at normal pressure is ~4 Hz, and only frequency components in this narrow spectral band can produce efficient excitation of the tuning fork vibration.

Referring initially to FIGS. 2 and 6–10, a number of different configurations for a tuning fork 30 are shown. Tuning fork 30 is preferably a two-pronged quartz fork having tines or prongs 32. When set vibrating, a tuning fork resonates at a constant, specific pitch or frequency. The pitch that a particular tuning fork generates depends upon the length of the two prongs 32, with two nodes (not shown) near the bend of the U.

In a preferred embodiment, tuning fork 30 is a standard watch tuning fork. A typical watch tuning fork has Q≈20,000 or higher when it is encapsulated in vacuum (e.g. timepiece applications) and Q≈8,000 at normal atmospheric pressure. Therefore, the corresponding energy accumulation time at atmospheric pressure is t≈250 ms, which is significantly greater than any practical gas-filled resonator can provide. The mode at this frequency corresponds to a symmetric vibration mode (e.g. the prongs move in opposite directions). The antisymmetric vibration is piezoelectrically inactive.

The following "Example" sections highlight the performance of QEPAS.

EXAMPLE

A commercially available tuning fork, such as might be used in a wristwatch, (tuning fork R38-32.768-KHZ-Raltron) is obtained. The overall tuning fork dimensions are 6 mm×1.4 mm×0.2 mm, with each prong being 3.8 mm long and 0.6 mm wide. The gap between the prongs is 0.2 mm.

As discussed above, several configurations for detecting the photoacoustic signal with a tuning fork 30 are shown in FIGS. 2 and 6–10 and observations using the present tuning fork will be described.

Figure 2:
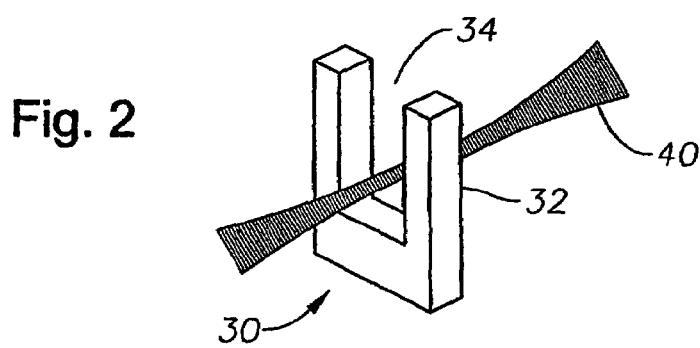
FIGS. 2 and 6–10 are schematic diagrams of different configurations for a tuning fork used in accordance with the principles of the present invention.
Figure 6:
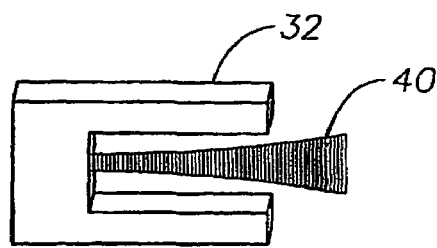
Figure 10:

FIGS. 2 and 6 correspond to aiming laser light 40 at the tuning fork 30 from different directions. In FIG. 2, the laser beam 40 is perpendicular to the tuning fork plane, while in FIG. 6 the laser beam 40 is in the tuning fork plane. Configuration 6 results in a longer effective pathlength but is more sensitive to alignment because the laser beam is directly contacting the fork.

Figure 7:
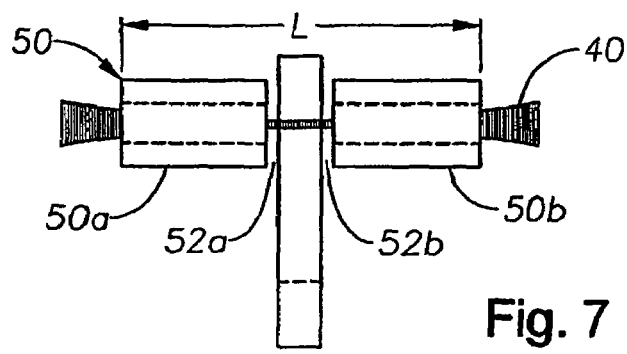

FIG. 7 presents a combination of a tuning fork 30 with an acoustic resonator or tube 50. Resonator 50 preferably comprises stainless steel capillary tubing of 1.59 mm outer diameter and 0.51 mm inner diameter. In some embodiments, resonator 50 comprises glass tubing. The overall length L of two tube pieces 50a, 50b plus the two gaps 52a, 52b between tubes and tuning fork 30 is 5.3 mm. This length L is equivalent to one-half of the sound wavelength at f=32,770 Hz, the resonant frequency of tuning fork 30, to travel. The tube centers (not shown) are preferably positioned 0.7 mm below the tuning fork opening 34 to ensure the most efficient tuning fork excitation.

Figure 8:
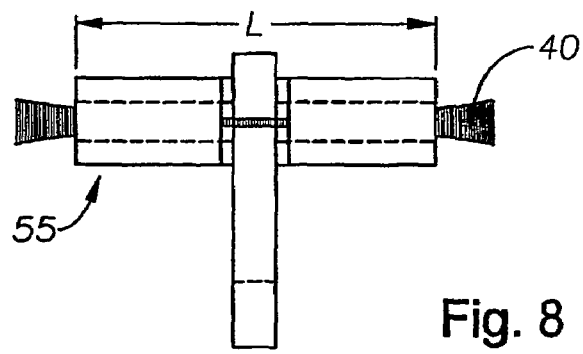
Figure 9:
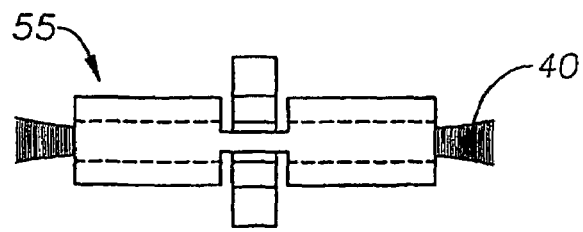

Similar to FIG. 7, FIG. 8 presents a combination of a tuning fork 30 with an acoustic resonator 55. However, in FIG. 8, resonator 55 is continuous through tuning fork 30; there are slots in resonator 55 to be received in tuning fork 30. FIG. 9 is a top view the tuning fork and acoustic resonator of FIG. 8. Overall length L is still preferably equivalent to one-half of the sound wavelength at f=32,770 Hz. In some embodiments it may be desirable for resonator 55 to comprise a full tube 56, while in other embodiments it may be desirable to attach a plurality of partial tubes or sails 57 to the tuning fork prongs to enhance the sound wave action (see FIG. 10).

A concern of using tuning forks is the coupling of the tuning fork to produce an electronic signal. For this purpose a simple operational amplifier-based transimpedence preamplifier circuit (see, for example, P. C. D. Hobbs, "Photodiode Front Ends: The Real Story", *Optics & Photonics News* 12, 44–47 (2001) incorporated herein by reference) with a feedback resistor of 4.4 Mohm was used. Thus, the piezoelectric signal was detected in the current mode (current detected when voltage across the tuning fork is kept at zero). Such a circuit minimizes the influence of any parasitic parallel capacitance by constantly keeping the voltage between the tuning fork electrodes close to zero.

Noise in the tuning fork coupled to a transimpedence amplifier has been investigated in detail by R. D. Grober et al in "Fundamental Limits to Force Detection Using Quartz Tuning Forks", *Review of Scientific Instruments* 71, 2776 (2000), incorporated herein by reference. The fundamental limitation of the tuning fork sensitivity arises from thermal excitation of its symmetric mode, i.e. the energy kT stored in its vibration. This excitation manifests itself as a peak in the noise spectrum centered at the tuning fork resonance frequency, f, and with a width defined by tuning fork Q-factor. This peak was observed using a network signal analyzer. A minor additional source of noise arises from the feedback resistor in the transimpedence amplifier circuit, creating a frequency-independent noise background.

Figure 3:
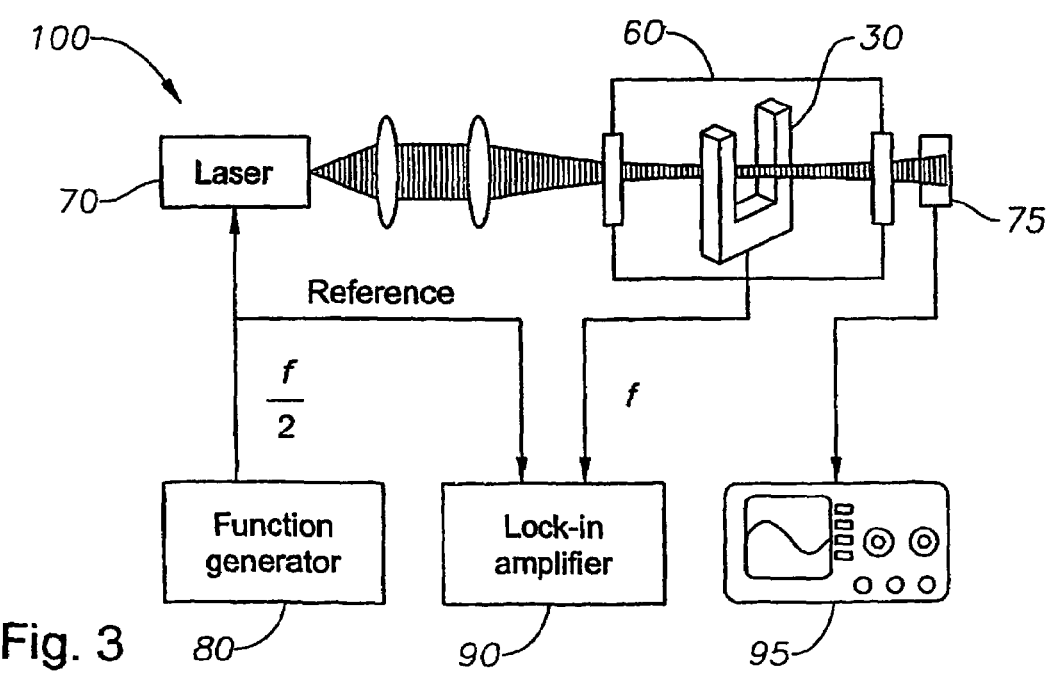
FIG. 3 is a schematic diagram of an experimental arrangement in accordance with the principles of the present invention.

Referring now to FIG. 3, an experimental arrangement 100 using the configuration of FIG. 2 is shown. Arrangement 100 includes a fluid cell 60 surrounding timing fork 30, a laser 70, an optional photodiode 75, a function generator 80, an amplifier 90, and an output device 95. Fluid cell 60 is a 5 cm long optical gas cell and laser 70 is a distributed feedback (DFB) diode laser. In a preferred embodiment, fluid cell 60, photodiode, and output device 95 are optional.

To investigate different aspects of QEPAS, fluid cell 60 was filled with air-methane mixtures of various concentration ratios. To excite a photoacoustic signal, laser 70 operating at $\lambda \sim 1.66$ µm was used. Laser 70 was tunable with current or temperature from 5997 to 6001 cm$^{-1}$, thus covering a number of rovibrational lines in a Q-branch of 2 v3 overtone of methane ($CH_4$).

The laser 70 temperature was generally set to +22.8° C. so that its frequency coincided with the peak absorption of the group of overlapping lines at 5999.5 cm$^{-1}$. Photodiode 75, located after fluid cell 60, can be used for accurate positioning of tuning fork 30 with respect to the laser beam, and also to detect $CH_4$ absorption lines for initial laser frequency calibration. The laser current was sinusoidally modulated at half the tuning fork resonant frequency, f, giving rise to wavelength (and amplitude) modulation at the same frequency (f/2). An absorption line in the gas was crossed twice during each modulation period, which resulted in acoustic waves generated at the tuning fork resonant frequency f, f being determined from the peak of the noise spectrum, described previously.

The tuning fork f was found to be pressure-dependent, linearly decreasing with increasing pressure at a rate of k=−8×10−3 Hz/Torr. The diode current modulation depth was adjusted to ensure maximum signal at f without strong deterioration of spectral resolution. The pressure in fluid cell 60 was generally set to 375 Torr total pressure to ensure a suitable spectral resolution. At this pressure Q≈13000 and the noise voltage at f after the transimpedence preamplifier was 1.1 µV/$\sqrt{Hz}$ ms. This measured noise is in good agreement with the experimental results and theoretical predictions of "Fundamental Limits to Force Detection Using Quartz Tuning Forks", *Review of Scientific Instruments* 71, 2776 (2000).

Goals of the experiments included: (1) verifying the local nature of the QEPAS sensing technique; (2) determining the most sensitive portion of the tuning fork shown in FIG. 2; and (3) establishing and comparing the QEPAS response for the different configurations shown in FIGS. 2 and 6–7.

Figure 4:
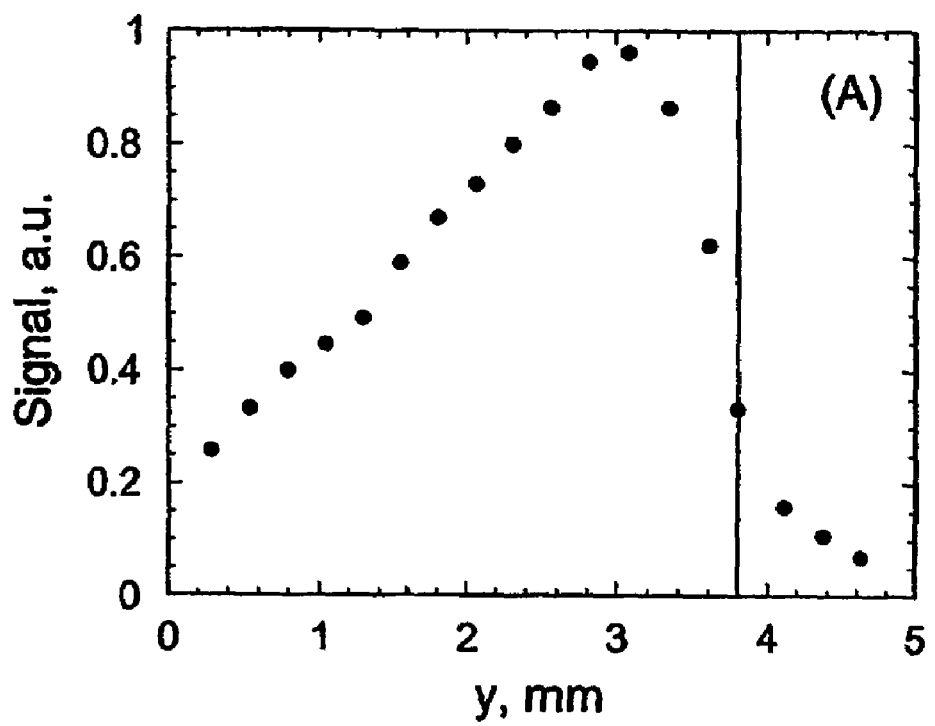
FIGS. 4A–B are graphs showing a detected photoacoustic signal as a function of laser focal spot position.
Figure 4:
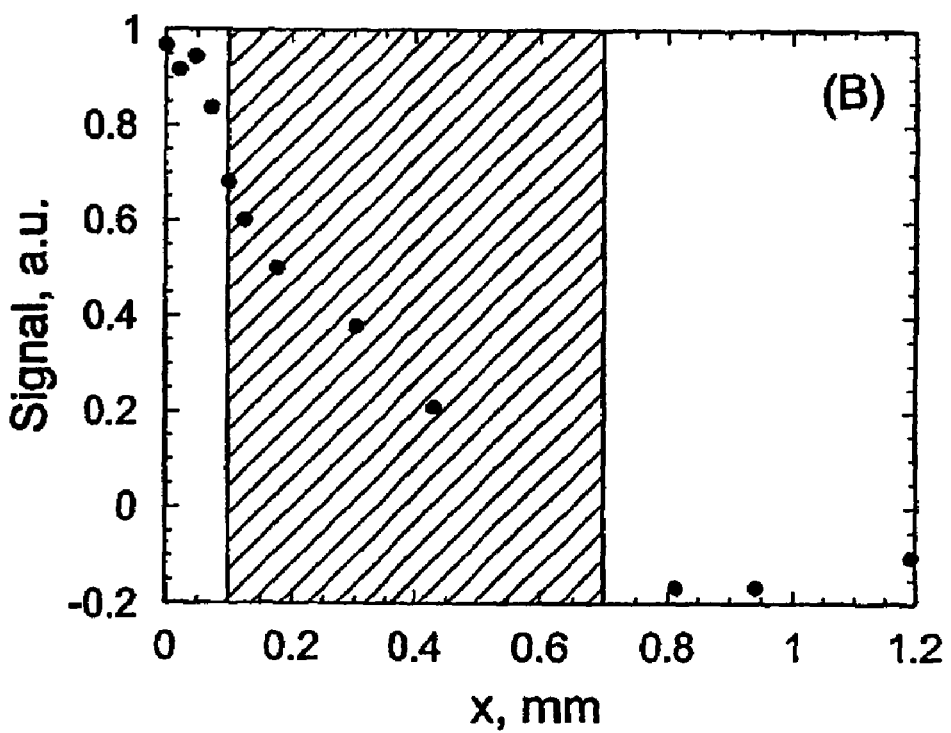

Referring now to FIGS. 3 and 4, the results of scanning the laser beam over the tuning fork are shown. For a high signal-to-noise ratio (SNR) and fast data acquisition, fluid cell 60 was filled with 100 Torr of CH4 and ambient air added to 1 atm total pressure with the lock-in time constant set to 300 ms.

In FIGS. 4A–B, the detected photoacoustic signal as a function of the laser focal spot position is shown, with the laser beam perpendicular to the tuning fork plane. The x-coordinate is the distance from the line parallel to the prongs and centered between them and the y-coordinate is the distance from the base of the prongs. In FIG. 4A, the focal spot is centered (x=0) between the prongs and the y coordinate is varied The horizontal scale origin is at the base of the prongs. The vertical line at 3.8 mm marks the location of the opening at the top of the tuning fork.

In FIG. 4B, the focal spot is scanned across the prongs starting from the center of the tuning fork. The distance y from the tuning fork base is constant and corresponds to the height of the maximum signal in FIG. 4A. The shaded area marks the region where the laser beam hits a tuning fork prong.

It was determined from the foregoing plots that the tuning fork response is highest (tuning fork is most sensitive) when the focal spot is centered between the tuning fork prongs and positioned approximately 0.7 mm below the tuning fork opening. When the focal spot is shifted to the area outside the tuning fork, the phase of its response is inverted, because the tuning fork prong closest to the laser beam is pushed by acoustic wave in the opposite direction. No laser-induced signal was observed at f if the laser wavelength was tuned off the absorption line or the cell filled with pure nitrogen; this was the case even when the laser beam directly hit the tuning fork prong or base.

Referring again to FIGS. 2–3 and 6–7 the noise level for all three configurations was the same, as determined by the fundamental limits set by thermal excitation of the tuning fork and a feedback resistor noise. To generate a photoacoustic signal, fluid cell 60 was filled with ambient air doped with 6.7% $CH_4$ at a total pressure of 375 Torr, providing a peak absorption coefficient $\alpha=1.71\times10-2$ cm$-1$ at $v=5999.49$ cm$-1$. Results for the voltage responsivity of the system to the molecular absorption and the detection limits for three of the configurations are presented in Table 1.

TABLE 1

Normalized response of the tuning fork-preamplifier unit
and normalized minimum (SNR = 1) detectable absorption
coefficient for FIGS. 2, 6 and 7

| Configuration | 2 | 6 | 7 |
|---|---|---|---|
| Responsivity (V/Wcm$^{-1}$) | 1.24 | 5.03 | 9.45 |
| Detectivity (Wcm$^{-1}$/Hz$^{1/2}$) | $8.8 \times 10^{-7}$ | $2.2 \times 10^{-7}$ | $1.2 \times 10^{-7}$ |

Figure 5:
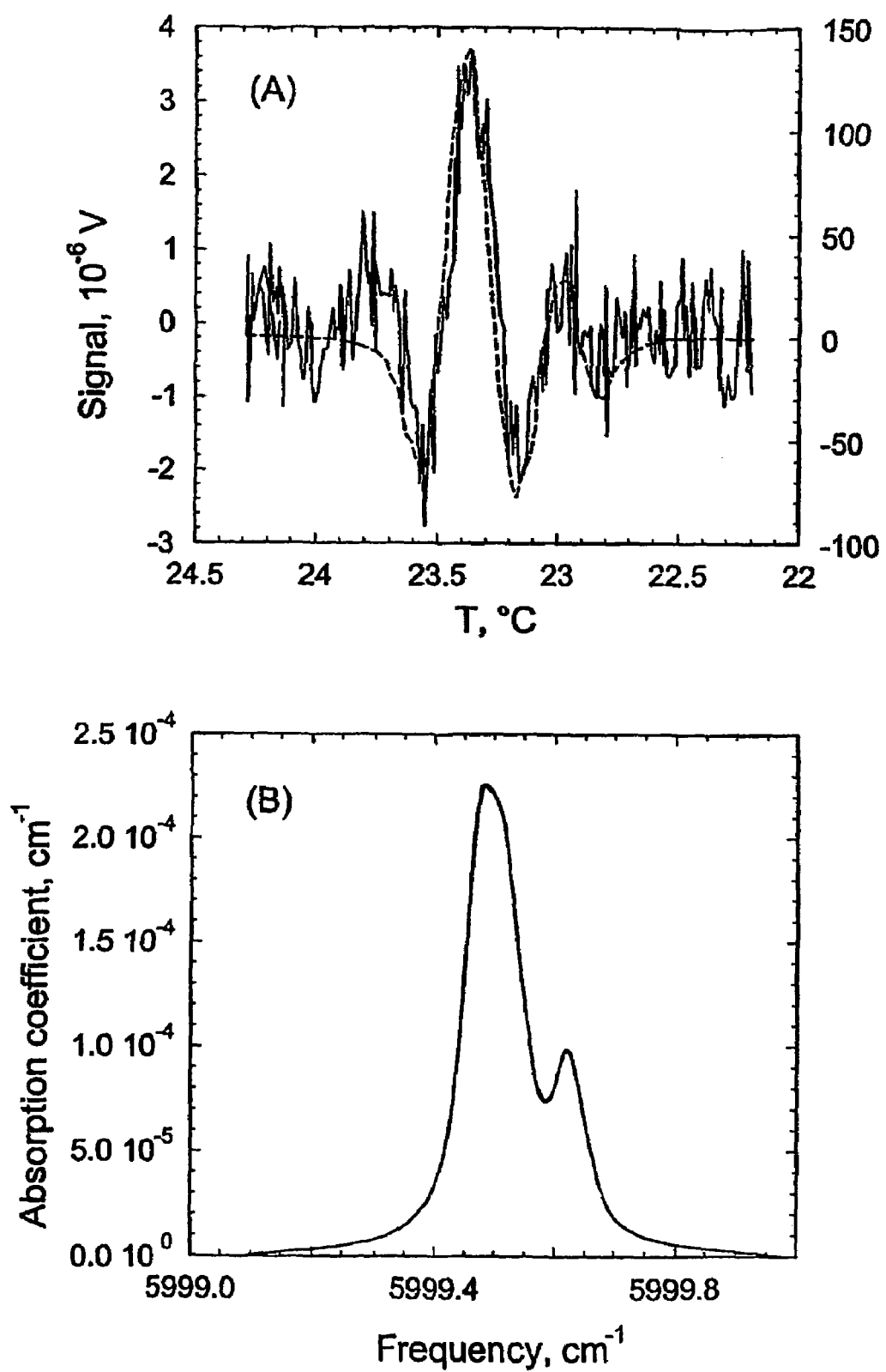
FIGS. 5A–B are graphs showing photoacoustic spectra acquired using a quartz-enhanced photoacoustic spectroscopy technique.

Two examples of actual photoacoustic spectra acquired with QEPAS technique in configuration of FIG. 6 are presented in FIG. 5A. These data were acquired with laser power ~2 mW and a lock-in amplifier time constant τ=1 s. The laser optical frequency was scanned by changing its temperature. The thick dashed line and thin solid line correspond respectively to 6.7% and 0.17% $CH_4$ concentration in ambient air at a total pressure of 375 Torr. The absorption for the lower concentration simulated using data from L. S. Rothman et al. in "The HITRAN Molecular Spectroscopic Database and HAWKS (HITRAN Atmospheric Workstation): 1996 Edition", *J. Quant. Spectrosc. Radiat. Transfer* 60, 665–710 (1998), is shown in FIG. 5B. As can be appreciated, signal scales linearly with concentration, and the detection limit at this low laser power is better than $10^{-4}$ cm$^{-1}$.

These results demonstrate that QEPAS is capable of providing detectivity levels for absorption comparable to that of conventional PAS with a much simpler and less delicate system.

It has been contemplated that QEPAS sensitivity can be further improved if a specially designed quartz crystal is used instead of a standard watch timing fork. For example, the tuning fork could be sized to provide a specific preferred resonant frequency. Other modifications of crystal-enhanced PAS are also contemplated where other means of detection of the crystal vibration are employed in place of the detection of the piezoelectric signal. For example, vibrational deformation of a crystal might be detected by means of stress-induced birefringence in the crystal or by modulation of an optical path (interferometric methods).

QEPAS units in accordance with the present invention preferably include a tuning fork and a preamplifier. These QEPAS units are very compact, inexpensive and immune to environmental acoustic noise. A set of such units may be used for multipoint gas-sensing applications. In a preferred embodiment, the central module of such a sensor will contain a laser and all the associated electronics, and the laser power could be delivered to each QEPAS sensor via optical fibers.

QEPAS also allows the spectroscopic analysis of extremely small gas samples, with the minimum sample volume ultimately being defined by the gas volume between the tuning fork prongs.

While preferred embodiments of this invention have been shown and described, modification thereof can be made by one skilled in the art without departing from the spirit or teaching of this invention. The embodiments described herein are exemplary only and are not limiting. Many variations and modifications of the compositions and methods are possible and are within the scope of this invention. Accordingly, the scope of protection is not limited to the embodiments described herein, but is only limited by the claims, the scope of which shall include all equivalents of the subject matter of the claims. In addition, the sequential recitation steps in the claims is not intended to require that the steps be performed in any particular order, or that any step be completed before commencement of another step.

What is claimed is:

1. A method for performing photoacoustic spectroscopy (PAS) of a sample, the method comprising:
   (a) providing a light source configured to introduce light having at least one wavelength into the sample such that at least one molecule within the sample is stimulated, generating an acoustic signal;
   (b) accumulating the acoustic signal in a resonant acoustic detector; and
   (c) displaying an output signal indicative of the acoustic signal, wherein the acoustic detector is a tuning fork and wherein the light passes between tines of the tuning fork.

2. The method according to claim 1 wherein the wavelength of the light in step (a) is selected such that the molecule resonates at the wavelength.

3. The method according to claim 1 wherein the light provided in step (a) is modulated at a resonant acoustic frequency f.

4. The method according to claim 3 wherein the acoustic detector resonates at the resonant acoustic frequency f.

5. The method according to claim 4 wherein the acoustic detector accumulates the acoustic signals during a predetermined number of oscillation periods Q.

6. The method according to claim 5 wherein Q and f are related by the equation t=Q/f with (being the time it takes the acoustic detector to accumulate one acoustic signal.

7. The method according to claim 6 wherein Q is less than 8,000.

8. The method according to claim 1, further including the step of converting said acoustic signal to an electric signal and amplifying at least one of the signals, prior to step (c).

9. The method according to claim 1 wherein the light source is a laser.

10. The method according to claim 1 wherein the acoustic detector comprises a low-loss crystal material shaped into a resonant element.

11. The method according to claim 10 wherein the material is piezoelectric quartz.

12. A photoacoustic spectroscopy (PAS) system for detecting an acoustic signal, the system comprising a light source and an acoustic detector, wherein the acoustic detector accumulates at least one resonant acoustic signal and emits an electrical signal corresponding to the acoustic signal, wherein the acoustic detector is a tuning fork and wherein light from the light source passes between tines of the tuning fork.

13. The system according to claim 12 further comprising a preamplifier connected to the acoustic detector, wherein the preamplifier amplifies at least one of the signals.

* * * * *

UNITED STATES PATENT AND TRADEMARK OFFICE
CERTIFICATE OF CORRECTION

| | |
|---|---|
| PATENT NO. | : 7,245,380 B2 |
| APPLICATION NO. | : 10/517177 |
| DATED | : July 17, 2007 |
| INVENTOR(S) | : Anatoliy A. Kosterev |

It is certified that error appears in the above-identified patent and that said Letters Patent is hereby corrected as shown below:

Col. 8, line 34, replace "(being" with -- t being --

Signed and Sealed this

Eighteenth Day of September, 2007

JON W. DUDAS
*Director of the United States Patent and Trademark Office*